(12) United States Patent
Kimura et al.

(10) Patent No.: US 8,273,087 B2
(45) Date of Patent: Sep. 25, 2012

(54) ULTRASONIC SURGICAL APPARATUS

(75) Inventors: Kenichi Kimura, Hachioji (JP);
Susumu Komagata, Ebina (JP); Hideto Yoshimine, Hachioji (JP); Manabu Ishikawa, Hachioji (JP)

(73) Assignee: Olympus Medical Systems Corp. (JP)

( * ) Notice: Subject to any disclaimer, the term of this patent is extended or adjusted under 35 U.S.C. 154(b) by 397 days.

(21) Appl. No.: 12/418,662

(22) Filed: Apr. 6, 2009

(65) Prior Publication Data

US 2009/0318944 A1 Dec. 24, 2009

Related U.S. Application Data

(60) Provisional application No. 61/073,896, filed on Jun. 19, 2008.

(51) Int. Cl.
*A61B 17/00* (2006.01)

(52) U.S. Cl. ............... 606/79; 606/83; 606/84; 606/169

(58) Field of Classification Search ............... 606/79, 606/83–85, 169
See application file for complete search history.

(56) References Cited

U.S. PATENT DOCUMENTS

| | | | | |
|---|---|---|---|---|
| 5,540,693 | A * | 7/1996 | Fisher | 606/79 |
| 6,117,152 | A | 9/2000 | Huitema | |
| 6,497,715 | B2 | 12/2002 | Satou | 606/169 |
| 6,511,493 | B1 * | 1/2003 | Moutafis et al. | 606/167 |
| 2001/0047182 | A1 | 11/2001 | Banko | |
| 2004/0147945 | A1 * | 7/2004 | Fritzsch | 606/169 |
| 2005/0143730 | A1 | 6/2005 | Novak et al. | |
| 2006/0253050 | A1 | 11/2006 | Yoshimine et al. | |

FOREIGN PATENT DOCUMENTS

| | | |
|---|---|---|
| EP | 0 591 619 A1 | 6/1993 |
| EP | 0 908 148 A1 | 4/1999 |
| EP | 0 908 150 A1 | 4/1999 |
| WO | WO 02/24084 A1 | 3/2002 |
| WO | WO 2007/025230 A2 | 3/2007 |

OTHER PUBLICATIONS

Letter from German associate dated Dec. 10, 2009 forwarding the Search Report dated Dec. 4, 2009 to Japanese associate, including discussion of relevancy thereof.
Search Report issued by European Patent Office in connection with corresponding application No. EP 09 00 5172.

* cited by examiner

*Primary Examiner* — Andrew Yang
(74) *Attorney, Agent, or Firm* — Ostrolenk Faber LLP

(57) ABSTRACT

An ultrasonic surgical instrument has an ultrasonic transducer unit having an ultrasonic transducer for producing ultrasonic vibration, a transmission member which connects the ultrasonic transducer in the proximal end side, and transmits the ultrasonic vibration produced by the ultrasonic transducer from the proximal end side to the distal end side, a sheath, in which the transmission member is inserted, having an open part on one side of the distal end side, and a treatment portion which is provided at the distal end of the transmission member, and exposed to the open part for carrying out a surgical treatment on an object part by the ultrasonic vibration transmitted from the transmission member. The ultrasonic surgical instrument cuts or shaves hard tissues.

5 Claims, 16 Drawing Sheets

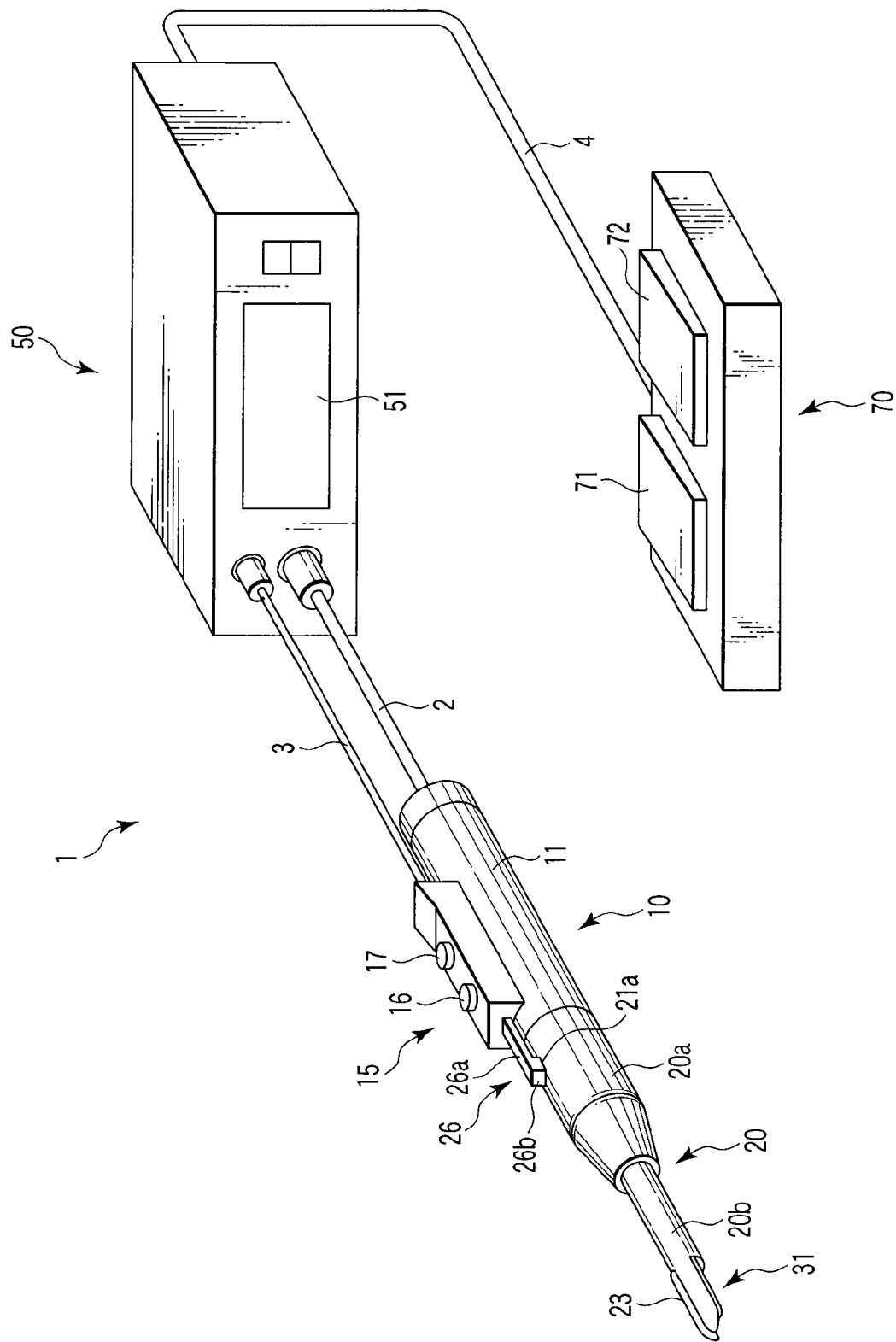
F I G. 1

A-A

B-B

B-B

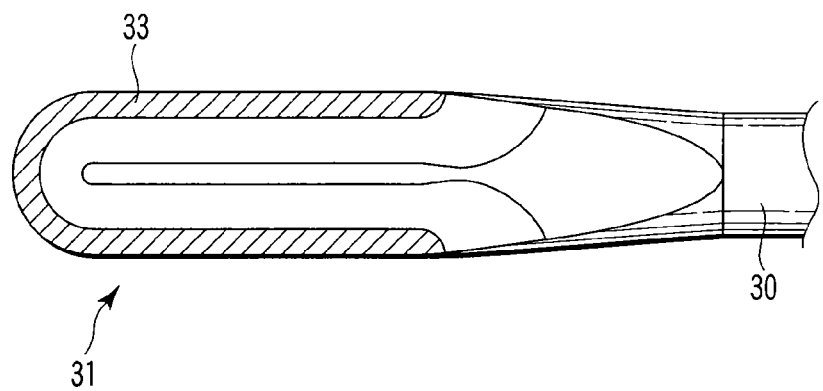
F I G. 9A
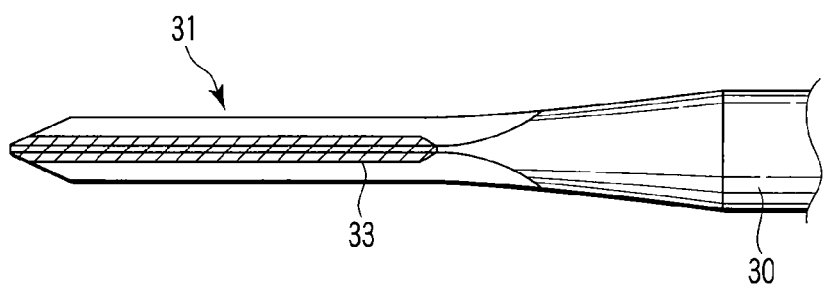
F I G. 9B
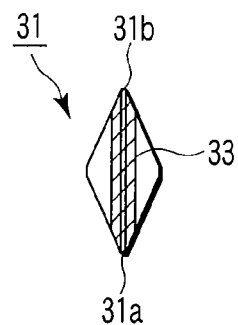
F I G. 9C

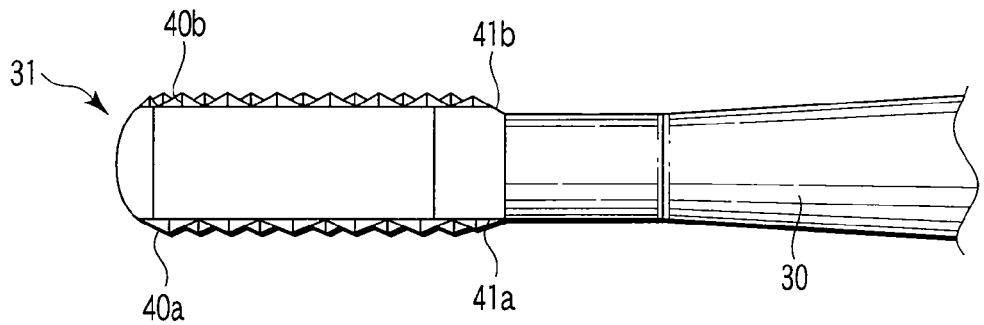
F I G. 12A
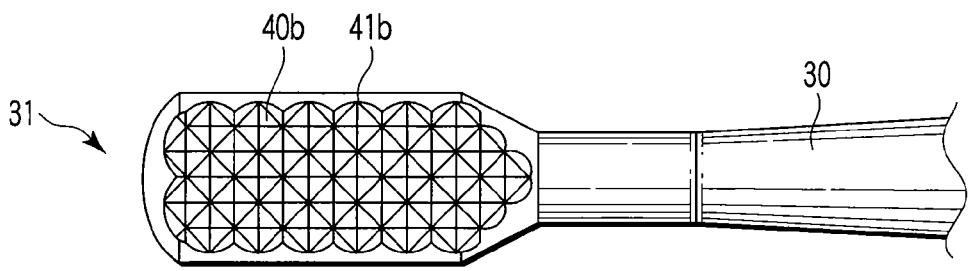
F I G. 12B
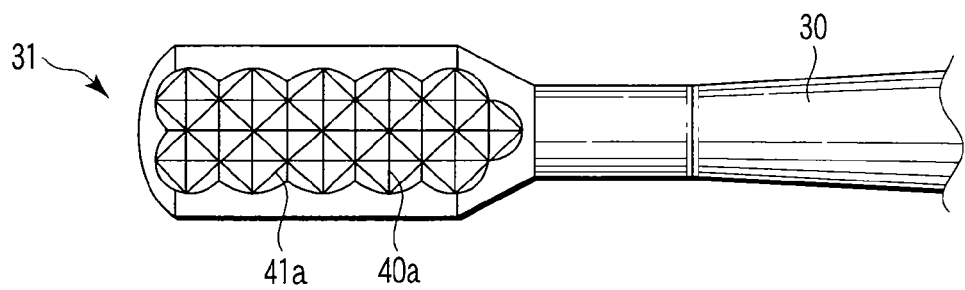
F I G. 12C

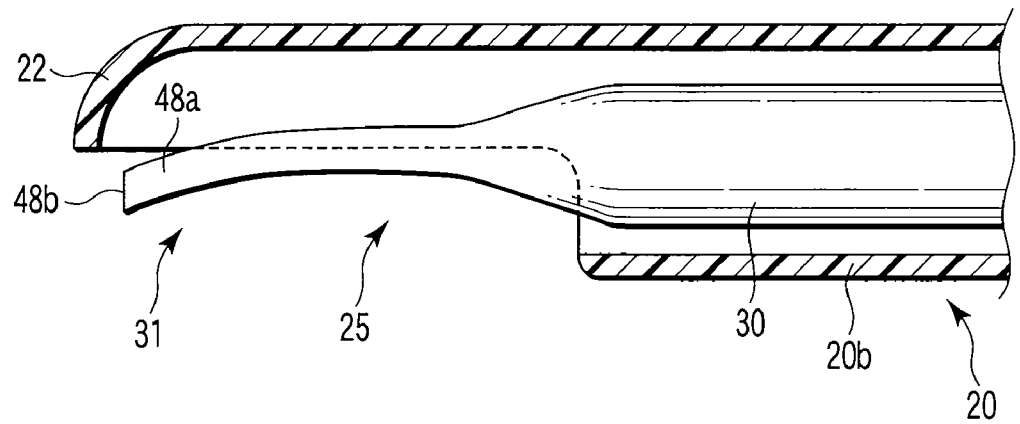
F I G. 19
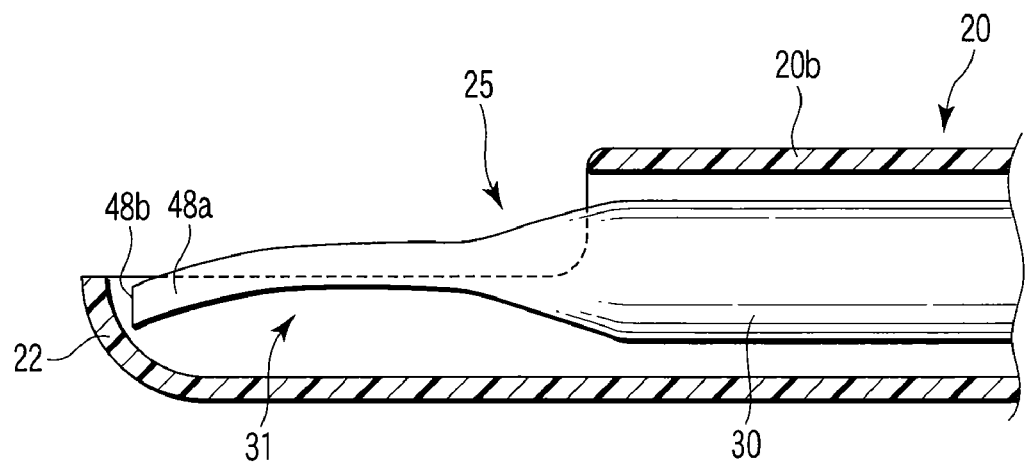
F I G. 20

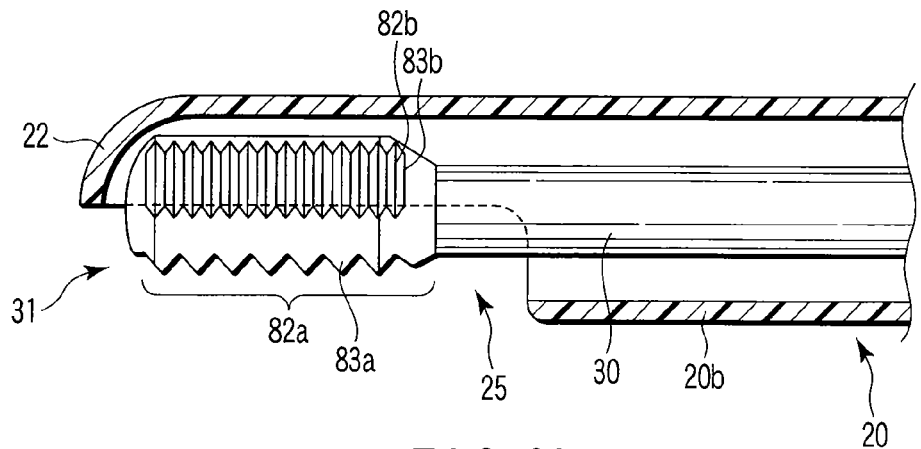
F I G. 23
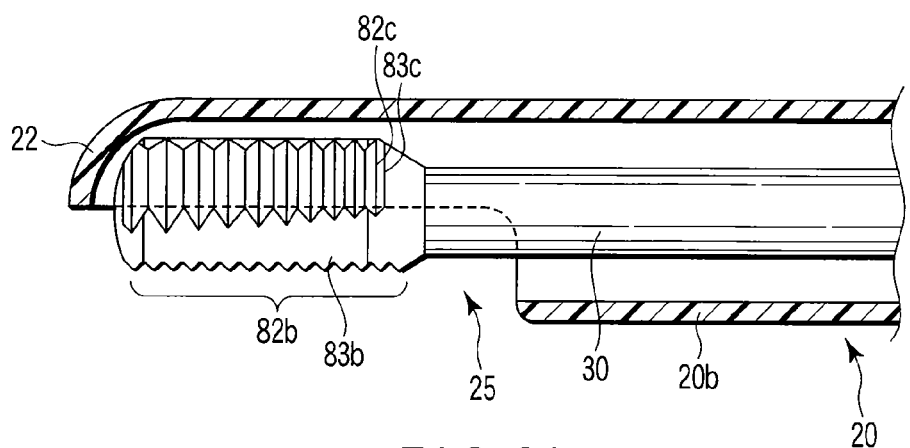
F I G. 24
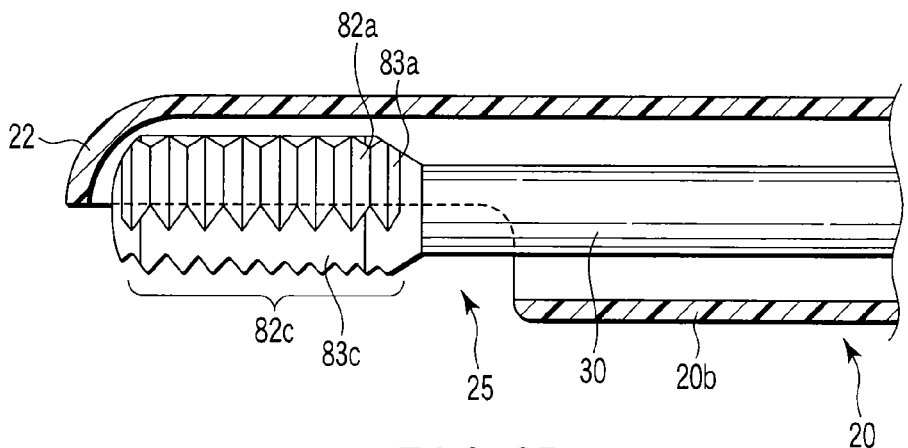
F I G. 25

ULTRASONIC SURGICAL APPARATUS

CROSS-REFERENCE TO RELATED APPLICATIONS

This application claims the benefit of U.S. Provisional Application No. 61/073,896, filed Jun. 19, 2008.

BACKGROUND OF THE INVENTION

1. Field of the Invention

The present invention relates to an ultrasonic orthopedic surgical instrument for carrying out a surgical treatment on bones.

2. Description of the Related Art

An instrument is generally used for cutting or shaving hard tissues such as bones and cartilages in orthopedic surgery. The instrument is a cold knife, a manual punch forceps, and a motor-driven shaver and drill, for example.

For example, U.S. Pat. No. 6,497,715 B2 discloses an ultrasonic hand piece, and an ultrasonic horn used for the hand piece. The ultrasonic horn is a constituent component of the ultrasonic hand piece. The ultrasonic horn has an operating part comprising at least one or more sides, and an edge part for scraping off minute bone tissues crushed by the operating part. The ultrasonic hand piece and ultrasonic horn, in an ultrasonic hand piece used for cutting hard tissues, prevents adverse effects caused by over-cutting with a scalpel, finely controls movement of a scalpel under a wide field of vision, and realizes exact cutting of hard tissues such as bones to meet an objective of surgery.

BRIEF SUMMARY OF THE INVENTION

It is an object of the present invention to provide an ultrasonic surgical instrument, which enables two or more treatments with one hand piece, and simplifies operations in surgery.

According to an aspect of the invention, there is provided an ultrasonic surgical instrument for cutting or shaving hard tissues, comprising an ultrasonic transducer unit having an ultrasonic transducer for producing ultrasonic vibration; a transmission member which connects the ultrasonic transducer in the proximal end side, and transmits the ultrasonic vibration produced by the ultrasonic transducer from the proximal end side to the distal end side; a sheath in which the transmission member is inserted, and has an open part on the side of the distal end side; and a treatment portion which is provided at the distal end of the transmission member, and exposed to the open part for carrying out a surgical treatment on an object part by the ultrasonic vibration transmitted from the transmission member.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic perspective view of an ultrasonic orthopedic surgical instrument according to a first embodiment of the invention;

FIG. 9A is a side view of a treatment portion in a second modification of the first embodiment;

FIG. 9B is a top view of the treatment portion shown in FIG. 9A;

FIG. 9C is a front view of the treatment portion shown in FIG. 9A;

FIG. 12A is a side view of a treatment portion according to a second embodiment;

FIG. 12B is a top view of the treatment portion shown in FIG. 12A;

FIG. 12C is a bottom view of the treatment portion shown in FIG. 12A;

FIG. 19 is a schematic diagram of peripheral parts of a treatment portion in a third modification of the second embodiment;

FIG. 20 is a schematic diagram of peripheral parts of the treatment portion with a distal end member moved from the state shown in FIG. 19;

FIG. 23 is a schematic diagram of peripheral parts of the treatment portion in the fourth modification of the second embodiment;

FIG. 24 is a schematic diagram of peripheral parts of the treatment portion in the fourth modification of the second embodiment; and FIG. 25 is a schematic diagram of peripheral parts of the treatment portion in the fourth modification of the second embodiment.

DETAILED DESCRIPTION OF THE INVENTION

Figure 2:
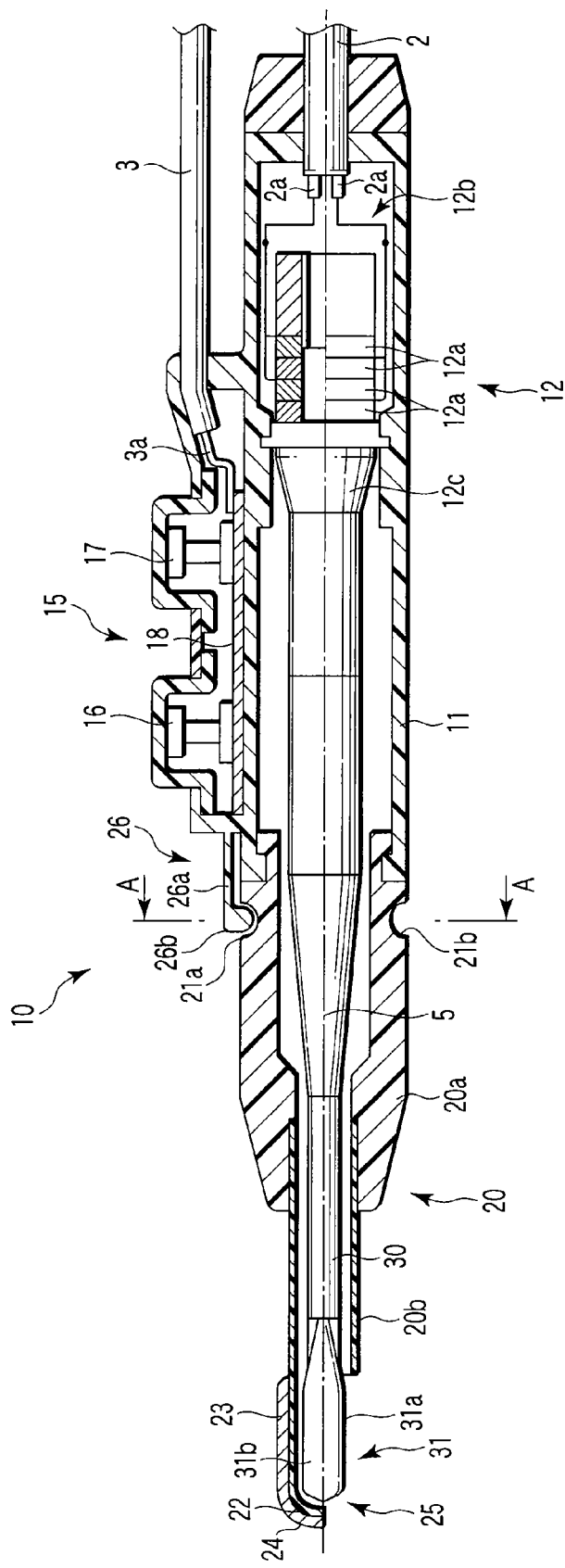
FIG. 2 is a sectional view of a hand piece.

Embodiments of the invention will be explained in detail hereinafter with reference to the accompanying drawings.

A first embodiment will be explained with reference to FIG. 1 to FIG. 7.

As shown in FIG. 1, an ultrasonic orthopedic surgical instrument 1 has a hand piece 10 for carrying out a surgical treatment on an object part in orthopedic surgery, for example, an ultrasonic vibration drive 50, and a foot switch 70. An object part means hard tissues such as bones and cartilages. Carrying out a treatment means cutting or shaving.

The hand piece 10 is connected to the ultrasonic vibration drive 50 through an output connecting cable 2 and a switch connecting cable 3. The ultrasonic vibration drive 50 is connected to the foot switch 70 through the switch connecting cable 4.

The hand piece 10 has a substantially cylindrical case 11 in the proximal end side. The output connecting cable 2 and switch connecting cable 4 are connected to the proximal end of the case 11.

As shown in FIG. 2, an ultrasonic transducer unit 12 for producing ultrasonic vibration is fixed inside the proximal end side of the case 11. The ultrasonic transducer unit 12 has an ultrasonic transducer 12b for producing ultrasonic vibration (e.g., vertical ultrasonic vibration), and a horn 12c which is provided forward of the ultrasonic transducer 12b in the direction of the longitudinal axis 5 of the case 11 (the probe 30), and amplifies the ultrasonic vibration produced by the ultrasonic transducer 12b.

The ultrasonic transducer 12b consists of a plurality of ring-shaped piezoelectric element 12a. The piezoelectric element 12a is a member to convert electrical energy into ultrasonic vibration. The electrical energy is produced by the ultrasonic vibration drive 50, supplied to the piezoelectric element 12a through a conductor 2a of the output connecting cable 2, and converted into ultrasonic vibration by the piezoelectric element 12a. More than one (four in this embodiment) piezoelectric elements 12a are closely provided in the direction of the longitudinal axis 5 of the case 11. The horn 12c is connected to the piezoelectric elements 12a arranged closest to the distal end.

The ultrasonic transducer 12b is fixed inside the proximal end side of the case 11. The ultrasonic transducer 12b is a bolt-clamped Langevin type transducer (BLT), for example.

The horn 12c is made of metallic material such as titanium, duralumin and stainless steel.

As shown in FIGS. 1 and 2, the case 11 is provided with a hand switch 15 on the outer periphery of the case 11. The hand switch 15 has a first switch 16, and a second switch 17. An electrical circuit board 18 is connected to the first and second switches 16 and 17. The electrical circuit board 18 is connected to a conductor 3a of the switch connecting cable 3. Thereby, electrical signals are transmitted from the first and second switches 16 and 17 to the ultrasonic vibration drive 50 through the electrical circuit board 18 and conductor 3a.

The case 11 is provided with a sheath 20 for inserting a probe 30 as a transmission member described later, in the distal end side. In other words, the sheath 20 covers the probe 30, and connects the distal end side of the case 11.

The sheath 20 has a main body 20a fixed to the case 11 movably in the peripheral direction of the longitudinal axis 5, and a distal end member 20b provided in one piece with the main body 20a at the distal end of the main body 20a. As the distal end member 20b is provided in one piece with the main body 20a, when the main body 20a rotates, the distal end member 20b rotates together with the main body 20a in the same direction. The distal end member 20b is made of transparent resin material such as polycarbonate and methacrylic resin, for example.

Figure 3:
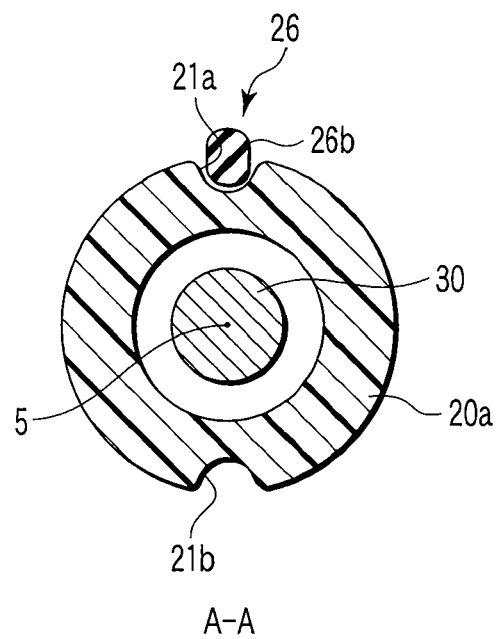
FIG. 3 is a cross sectional view of a main body taken along line A-A in FIG. 2.

The main body 20a is formed like a hollow cylinder. As shown in FIGS. 2 and 3, the main body 20a has recesses 21a and 21b on the periphery of the main body 20a. As shown in FIG. 3, the recesses 21a and 21b are provided symmetrical to each other with respect to the longitudinal axis 5 of the case 11.

The distal end member 20b is formed like a hollow cylinder. The distal end member 20b has a semiround wall-like part 22 at its distal end. The wall-like part 22 is the outer peripheral portion of the distal end member 20b. The wall-like part 22 is formed in one piece with a treatment device for carrying out a surgical treatment on an object part by cutting or shaving. The treatment device is a cold knife 23, for example. The cold knife 23 is made of metallic material such as stainless steel. The front end of the cold knife 23 is formed as an edge 24 for cutting or shaving an object part.

The distal end member 20b has, in one side, an open part 25 formed symmetrically to the wall-like part 22 with respect to the longitudinal axis 5 of the case 11. The open part 25 will be explained later.

Namely, the sheath 20 permits insertion of the probe 30, and has the open part 25 in one side of the distal end member 20b, that is, the distal end side of the sheath 20. The open part 25 is a notch, for example, formed in one side of the distal end member 20b, and is opened to one side of the distal end member 20b. The open part 25 is shaped like a semicircular cylinder. Namely, the sheath 20 has the substantially semicircular open part 25 on one side of the distal end member 20b. The sheath 20 has a treatment device (the cold knife 23) for carrying out a surgical treatment on an object part by cutting or shaving. The sheath 20 is rotationally movable in the peripheral direction of the probe 30 insertion direction (the direction of the longitudinal axis 5) to the probe 30.

The case 11 is provided with a rotation stopper member 26 for selectively determining the rotation position of the sheath 20 (the main body 20a) in the distal end side of the case 11. The rotation stopper member 26 is provided in one piece with the case 11 in the forward of the first switch 16 in the direction of the longitudinal axis 5. The rotation stopper member 26 has an elastic deformable arm 26a, and a stopper 26b fixed to the front end of the arm 26a. The stopper 26b fits in one of the recesses 21a and 21b when the sheath 20 (the main body 20a) is rotationally moved, thereby determining the rotation position of the sheath 20 (the main body 20a). The arm 26a, stopper 26b, and recesses 21a and 21b form a positioning mechanism for selectively determining a position of rotational movement of the sheath 20.

At the distal end of the horn 12c, the probe 30 is provided just like inserting in the case 11 and sheath 20 (the hollow cylindrical main body 20a and distal end member 20b). The probe 30 is a transmission member to transmit the ultrasonic vibration amplified by the horn 12c to the distal end side of the hand piece 10. The probe 30 is removably fixed to the horn 12c with a screw, for example. Namely, the probe 30 connects the ultrasonic transducer 12b through the horn 12c in the proximal end side of the probe 30, and transmits the ultrasonic vibration produced by the ultrasonic transducer 12b, from the proximal end side to the distal end side of the probe 30 (the distal end side of the hand piece 10).

The probe 30 is made of metallic material such as titanium, duralumin, and stainless steel, like the horn 12c.

In the relationship between the sheath 20 and probe 30, the sheath 20 is movable in the peripheral direction of the probe 30 insertion direction (the direction of the longitudinal axis 5) to the probe 30. Namely, the probe 30 is fixed, and the sheath 20 covering the probe 30 is rotationally moved.

The distal end of the probe 30 is extended to the part close to the wall-like part 22. The distal end of the probe 30 is provided with a treatment portion 31 for carrying out a surgical treatment on an object part by using ultrasonic vibration produced by the ultrasonic transducer 12b and transmitted from the probe 30, when the distal end is exposed to the open part 25. The treatment portion 31 is shaped substantially flat. The treatment portion 31 is formed like a blade having edges on the periphery.

The treatment portion 31 has a first edge 31a corresponding to the recess 21a, and a second edge 31b corresponding to the recess 21b.

Figure 4:
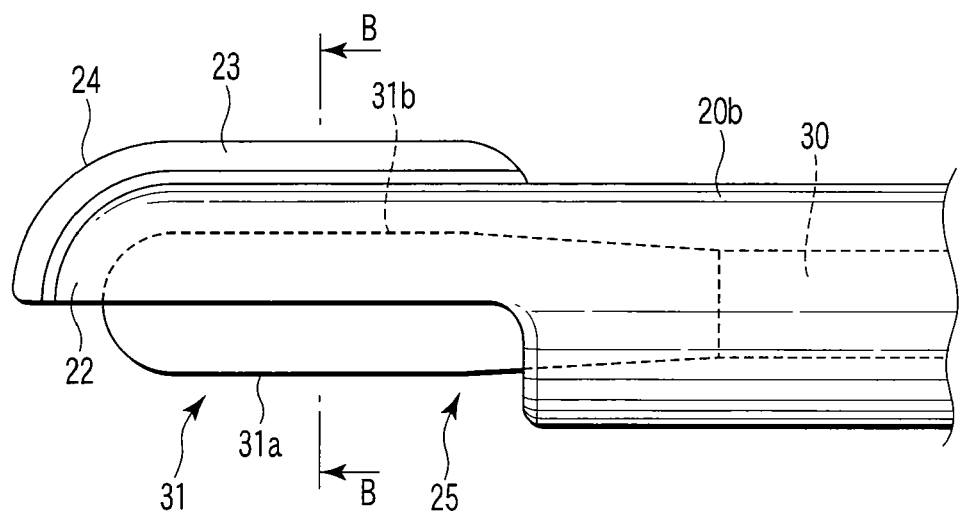
FIG. 4 is a side view of peripheral parts of a treatment portion.
Figure 6:
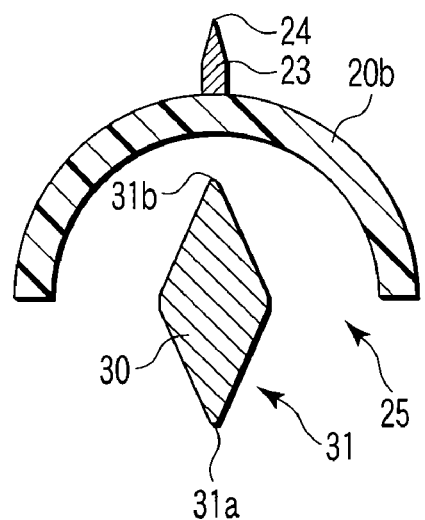
FIG. 6 is a cross sectional view of the treatment portion taken along line B-B in FIG. 4.
Figure 7:
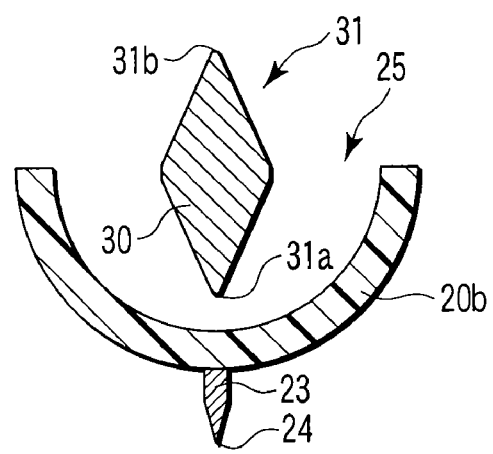
FIG. 7 is a cross sectional view of the treatment portion with a distal end member moved from the state shown in FIG. 6.

As described above, when the sheath 20 is rotationally moved around the probe 30, the stopper 26b fits in the recess 21a as shown in FIGS. 2 and 3. Thereby, the first edge 31a is exposed to the open part 25, and the second edge 31b is retracted into the sheath 20 (the distal end member 20b), as shown in FIGS. 4 and 6. When the sheath 20 is rotationally moved around the probe 30, and the stopper 26b fits in the recess 21b, the first edge 31a is retracted into the sheath 20 (the distal end member 20b), and the second edge 31b is exposed to the open part 25, as shown in FIG. 7. The treatment portion 31 does not contact the distal end member 20b when it is rotationally moved.

When one of the first and second edges 31a and 31b contacts an object part, the treatment portion 31 operates on the object part by ultrasonic vibration.

The ultrasonic vibration drive 50 is provided with a setting unit 51 for setting conditions for output of ultrasonic vibration. The setting unit 51 is a display panel, for example.

The foot switch 70 has a first pedal switch 71 corresponding to the first switch 16, and a second pedal switch 72 corresponding to the second switch 17.

In this embodiment, the setting unit 51 sets the above output conditions. One output condition is that an electric current of 70% of a maximum output condition, for example, is supplied, when one of the first switch 16 and first pedal switch 71 is turned on. The other output condition is that an electric current of 100% of a maximum output condition is supplied, when one of the second switch 17 and second pedal switch 72 is turned on. Namely, the setting unit 51 sets and displays these output conditions. Of course, the output condition set by the first switch 16 or the first pedal switch 71 (supplying 70% of a maximum current) and the output condition set by the second switch 17 or the second pedal switch 72 (supplying 100% of a maximum current) may be reversed. The values of supplied currents are adjustable.

Next, an explanation will be given of operating treatments in this embodiment.

The setting unit 51 is operated, and output conditions are set. As described above, the output conditions are that an electric current of 70% of a maximum output condition, for example, is supplied, when one of the first switch 16 and first pedal switch 71 is turned on, and an electric current of 100% of a maximum output condition is supplied, when one of the second switch 17 and second pedal switch 72 is turned on. When the output condition setting is completed, the treatment portion 31 contacts an object part of a living body tissue.

When the first switch 16 or first pedal switch 71 is operated, electrical energy corresponding to the value set by the setting unit 51 (70% of a maximum current) is output by the ultrasonic vibration drive 50.

When the second switch 17 or second pedal switch 72 is operated, electrical energy corresponding to the value set by the setting unit 51 (100% of a maximum output condition) is output by the ultrasonic vibration drive 50.

When the first switch 16 is operated, a signal indicating that the ultrasonic vibration drive 50 produces 70% of a maximum current is output to the ultrasonic vibration drive 50 through the electrical circuit board 18 and conductor 3a. This is similar when the second switch 17 is operated.

When the first pedal switch 71 is operated, a signal indicating that the ultrasonic vibration drive 50 produces 70% of a maximum current is output to the ultrasonic vibration drive 50 through the switch connecting cable 4. This is similar when the second pedal switch 72 is operated.

The electrical energy produced as above is supplied from the ultrasonic vibration drive 50 to the piezoelectric element 12a through the conductor 2a, and converted into ultrasonic vibration in the piezoelectric element 12a. The ultrasonic vibration is amplified by the horn 12c, and transmitted to the probe 30. At this time, the ultrasonic vibration is transmitted from the probe 30 to an object part through the treatment portion 31. Namely, the ultrasonic vibration is transmitted from the proximal end to the distal end of the probe 30. Thereby, the treatment portion 31 operates on an object part by the ultrasonic vibration.

The ultrasonic transducer 12b is driven by constant-current control, and the amplitude x (peak-to-peak value) of the ultrasonic vibration is kept constant in the treatment portion 31.

The amplitude x can be calculated by the following equation, based on a vibration velocity V in the treatment portion 31, and a resonance frequency fr of ultrasonic vibration.

$$X = V/\pi/\text{fr}$$

For example, under the 100% output condition, the vibration velocity V is preferably set to 7.4 m/s-22.1 m/s.

Therefore, the amplitude x under the 100% output condition is preferably set to 100-300 μm when the resonance frequency fr is 23.5 kHz, according to the above equation based on the values of the vibration velocity V and resonance frequency fr.

When the resonance frequency fr is 47 kHz, the amplitude x under the 100% output condition, for example, is preferably set to 50-150 μm.

In the states shown in FIGS. 2 and 3, when the stopper 26b fits in the recess 21a, the first edge 31a is exposed to the open part 25 as shown in FIG. 6, and the second edge 31b is retracted into the distal end member 20b. In this state, the first edge 31a contacts an object part, and repeatedly operates on the object part by ultrasonic vibration. The strength of the ultrasonic vibration is different depending on the above output conditions and equation, that is, whether the first switch 16 or first pedal switch 71, or the second switch 17 or second pedal switch 72 is selected.

These switches and pedal switches are desirably selected according to an object part to be operated on.

The first edge 31a may be worn or damaged by repetition of an ultrasonic treatment or contact to other metallic surgical device during ultrasonic vibration. In such a case, when the sheath 20 (the main body 20a) is manually turned around the case 11, for example, the arm 26a is deformed toward the outside of the main body 20a, and the stopper comes off the recess 21a. When the sheath 20 (the main body 20a) is rotationally moved about 180 degrees in the peripheral direction of the longitudinal axis 5 of the case 11 from the state shown in FIGS. 2 and 3 with respect to the case 11 and probe 30, the arm 26a recovers from the deformed state, and the stopper 26b fits in the recess 21b. When the main body 20a is rotationally moved, the distal end member 20b is rotationally moved in the same direction as the main body 20a.

Then, as shown in FIG. 7, the first edge 31a is retracted into the distal end member 20b, and the second edge 31b is exposed to the open part 25.

Even if the first edge 31a is damaged, the second edge 31b takes over the treatment carried out on an object part.

The cold knife 23 sharply cuts or shaves an object part, when it is pressed to an object part.

As described above, in this embodiment, when the sheath 20 (the main body 20a) is rotationally moved around the case 11, one edge (e.g., the first edge 31a) worn, damaged and decreased in performance is replaced by the other edge (e.g., the second edge 31b) not worn, damaged, and decreased in performance, without replacing the hand piece 10. Therefore, in this embodiment, even if one edge is worn and damaged, it is replaced by the other edge, and surgery can be smoothly continued.

Further, in this embodiment, an object part can be finely and exactly operated on the treatment portion 31 (the first and second edges 31a and 31b) using ultrasonic vibration.

An object part can also be finely and sharply operated on (cut or shaved) by the cold knife 23 when it is pressed to the object part.

As described above, in this embodiment, when an object part is operated on in orthopedic surgery, two or more kinds of treatment are possible by using the treatment portion 31 and cold knife 23 in one hand piece 10. The number of exchanging the hand piece 10 can be decreased depending on the kinds of treatment, and operations in surgery can be simplified.

The hand piece 10 of this embodiment is suitable for cutting and shaving hard tissues such as bones and cartilages in orthopedic surgery, particularly suitable for surgery for shaving a hip cup edge in a hip joint disease. As described above, the cold knife 23 can quickly and sharply cut or shave a damaged object part (e.g., a joint lip). The ultrasonically vibrating treatment portion 31 can remove a damaged object part (e.g., a joint lip), and can finely and exactly cut a hip cup edge.

In this embodiment, the probe 30 uses vertical ultrasonic vibration. A probe is not limited to this type. The probe 30 may be configured to use a combination of vertical and twisted ultrasonic vibrations.

Figure 8A:
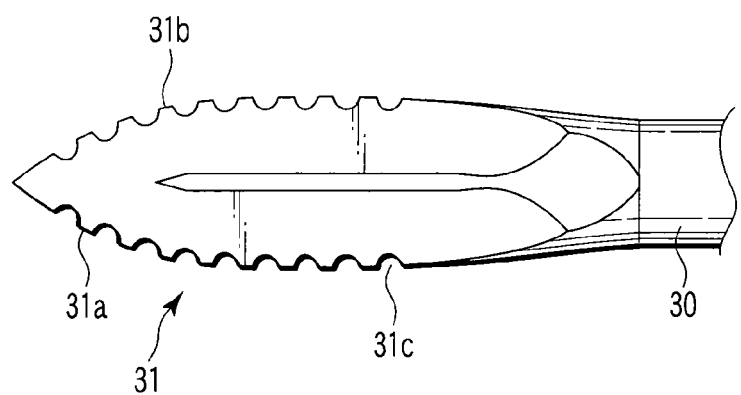
FIG. 8A is a side view of a treatment portion in a first modification of the first embodiment.
Figure 8B:
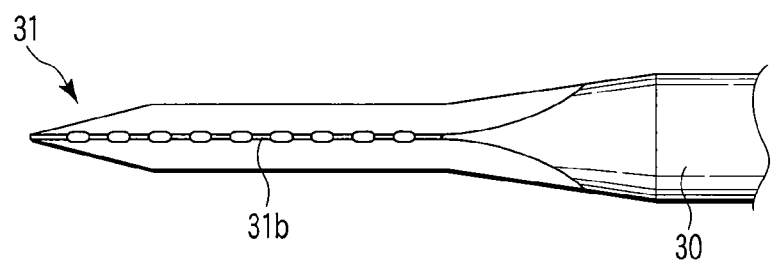
FIG. 8B is a top view of the treatment portion shown in FIG. 8A.
Figure 8C:
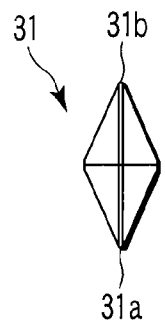
FIG. 8C is a front view of the treatment portion shown in FIG. 8A.

Next, a first modification of the embodiment will be explained with reference to FIGS. 8A to 8C.

The shape of the treatment portion 31 of this modification is different from the treatment portion 31 of the first embodiment. The treatment portion 31 of this modification is substantially flat with a pointed distal end. A first edge 31a and a second edge 31b have semicircular recesses 31c at equal intervals along their edges. The radius of the recess 31c is 0.2-0.6 mm. A pitch between adjacent recesses 31c is 0.5-2 mm.

Therefore, this modification can provide the same operations and effects as those of the first embodiment.

Next, a second modification of the embodiment will be explained with reference to FIGS. 9A to 9C.

The shape of the treatment portion 31 of this modification is similar to the treatment portion 31 of the first embodiment. The treatment portion 31 of this modification has a hard titanium nitride coating layer 33 formed by PVD or CVD along the edge. The coating layer 33 is formed in a desired distance from the edge, for example, in a range of 1 mm from the edge toward the inside of the treatment portion 31.

In this modification, as the coating layer 33 is formed, the durability of the treatment portion 31 to wearing and damages is improved. Further, in this embodiment, the degree of wearing and damages of the treatment portion 31 can be easily and visually confirmed from the condition of the coating layer 33 (e.g., whether or not the coating layer 33 is peeled off the treatment portion 31).

Further, in this modification, the cutting depth in an object part can be easily controlled by using the range of the coating layer 33 as a guide. Therefore, this embodiment enables surgery with higher accuracy.

Figure 10:
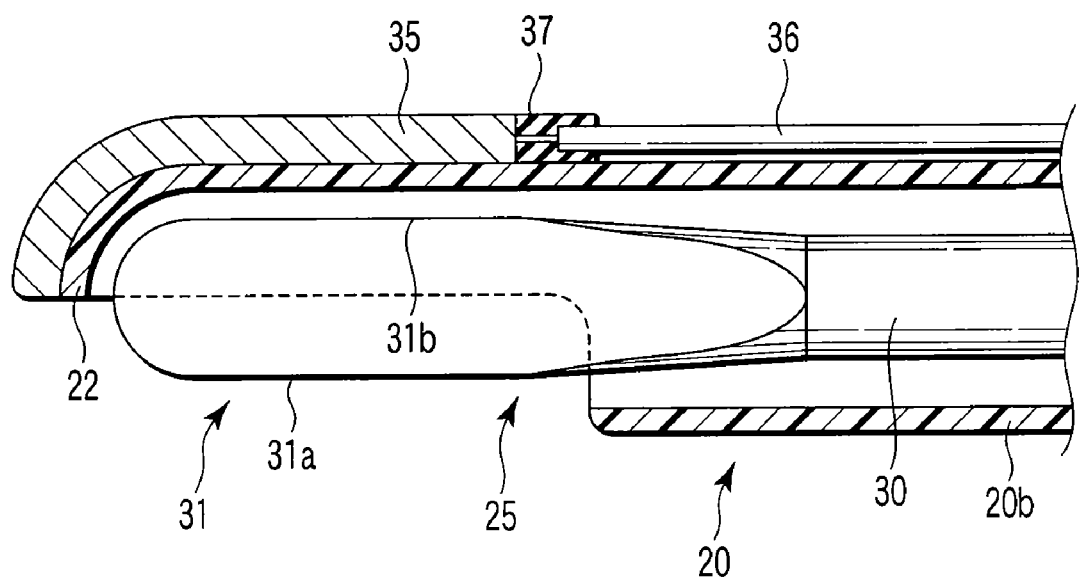
FIG. 10 is a schematic diagram of peripheral parts of a treatment portion in a third modification of the first embodiment.

Next, a third modification of the embodiment will be explained with reference to FIG. 10.

The distal end periphery of the wall-like part 22 of this modification is formed in one piece with a knife electrode 35, instead of the cold knife 23. The knife electrode 35 is made of conductive metallic material such as stainless steel. The rear end of the knife electrode 35 is connected to one end of a high-frequency output connecting cable 36. Insulating material 37 covers the connected portion of the rear end of the knife electrode 35 and one end of the high-frequency output connecting cable 36. The other end of the high-frequency output connecting cable 36 is connected to a not-shown high-frequency drive. Therefore, the knife electrode 35 functions as a monopolar electrode for outputting a high frequency. Namely, the knife electrode 35 functions as a high frequency electrode.

As described above, in this modification, the knife electrode 35 is used, and the knife electrode 35 is made to contact an object part of a living body tissue, to apply a high-frequency current to the object part, thereby cutting off a living tissue in a coagulated state.

Next, a second embodiment of the invention will be explained with reference to FIGS. 11 to 14. The same components as those of the first embodiment and its modifications are denoted by the same reference numbers, and an explanation thereof is omitted here.

In this embodiment, a sheath 20 is not provided with a cold knife 23 or a knife electrode 35. A treatment portion 31 of this embodiment has a first treatment surface 41a having square pyramid-shaped serrations 40a, and a second treatment surface 41b having square pyramid-shaped serrations 40b smaller than the serrations 40a. The first treatment surface 41a is substantially symmetrical to the second treatment surface 41b in the direction of the longitudinal axis 5.

As the serrations 40a are larger than the serrations 40b, the first treatment surface 41a is used for rough cutting of an object part, and the second treatment surface 41b is used for finish cutting.

As described above, the treatment portion 31 has two or more (plural) treatment surfaces (the first and second treatment surfaces 41a and 41b) in the peripheral direction of the probe 30 insertion direction (the longitudinal axis 5). Further, as the serrations 40a and 40b are different in size, the treatment portion 31 has two or more different shape treatment surfaces.

Figure 11:
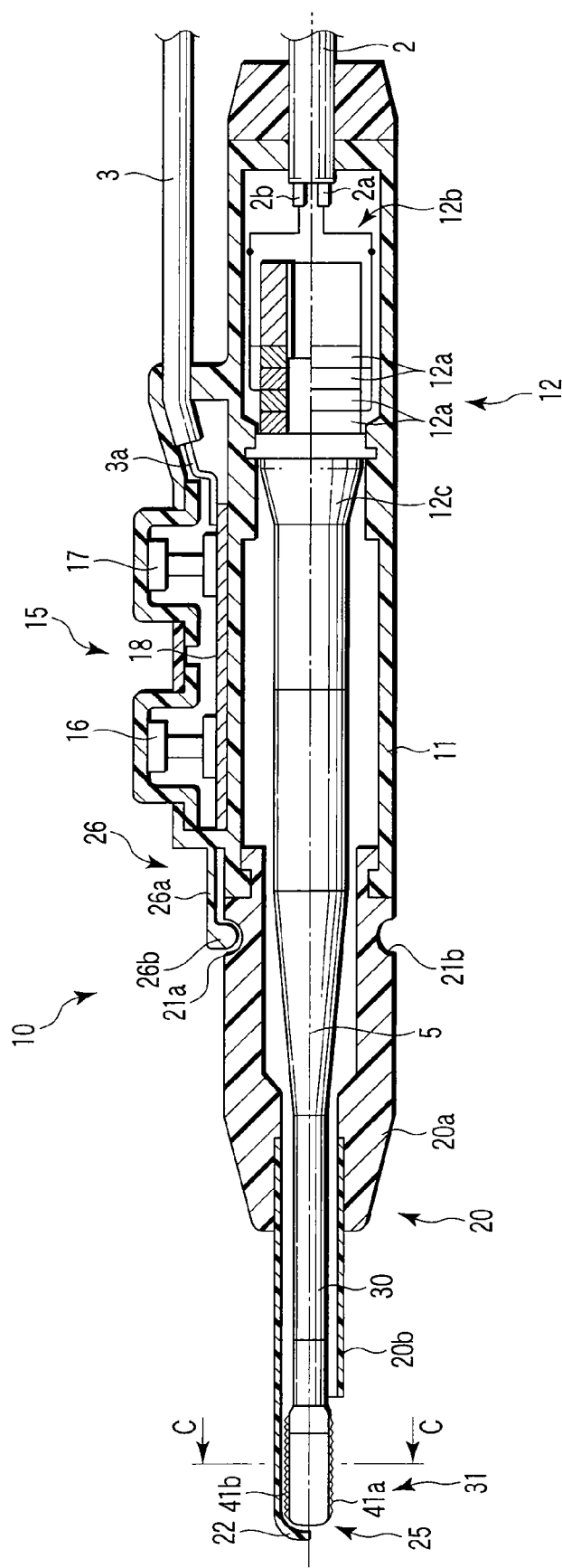
FIG. 11 is a sectional view of a hand piece according to a second embodiment of the invention.
Figure 13:
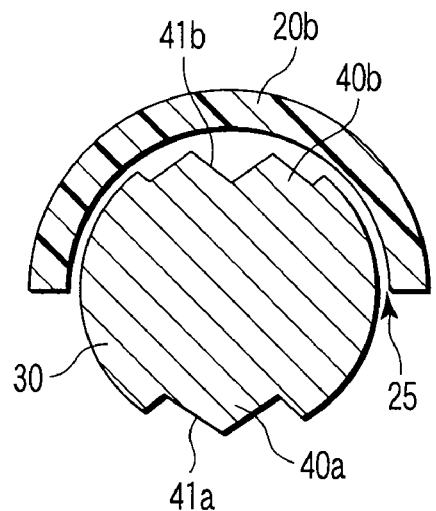
FIG. 13 is a cross sectional view of the treatment portion taken along line C-C in FIG. 11.

In this embodiment, when a stopper 26b fits in a recess 21a as shown in FIG. 11, the first treatment surface 41a is exposed to an open part 25, and the second treatment surface 41b is retracted into a distal end member 20b, as shown in FIGS. 11 and 13. When a sheath 20 is rotationally moved around a probe 30 and the stopper 26b fits in a recess 21b, the first treatment surface 41a is retracted into the distal end member 20b, and the second treatment surface 41b is exposed to the open part 25.

Next, an explanation will be given of operating treatments in this embodiment. The treatments other than those explained here are almost the same as those in the first embodiment, and detailed explanation thereof is omitted.

As shown in FIGS. 11 and 13, the first treatment surface 41a is exposed to the open part 25. In this state, the first treatment surface 41a is made to contact an object part of a living body tissue. When the probe 30 ultrasonically vibrates, the first treatment surface 41a ultrasonically operates on the contacting object part.

The first treatment surface 41a has the serrations 40a larger than the serrations 40b, and is used for rough cutting of the surface of a joint and cartilage.

Figure 14:
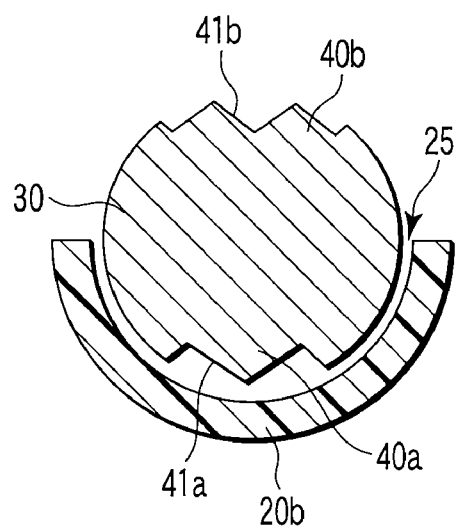
FIG. 14 is a cross sectional view of the treatment portion with a distal end member moved from the state shown in FIG. 13.

Further, as explained in the first embodiment, when the sheath 20 (the main body 20a) is moved about 180° around the case 11 or probe 30 from the states shown in FIGS. 11 and 13, the second treatment surface 41b is exposed to the open part 25 as shown in FIG. 14. In this state, the second treatment surface 41b is made to contact an object part of a living body tissue. When the probe 30 ultrasonically vibrates, the second treatment surface 41b ultrasonically operates on the contacting object part.

The second treatment surface 41b has the serrations 40b smaller than the serrations 40a, and is used for finish cutting of the surface of a joint and cartilage.

As described above, in this embodiment, the first treatment surface 41a is used for rough cutting of the surface of a joint and cartilage, the sheath 20 is moved about 180° as in the first embodiment, and the second treatment surface 41b is used for finish cutting of the surface of a joint and cartilage.

Namely, in this embodiment, two or more kinds of treatment (rough cutting and finish cutting) can be carried out by the first treatment surface 41a and the second treatment surface 41b by moving the sheath 20 around the case 11. Therefore, the number of exchanging the hand piece 10 can be decreased depending on the kinds of treatment, and operations in surgery can be simplified.

The hand piece 10 of this embodiment is suitable for cutting or shaving hard tissues such as bones and cartilages in orthopedic surgery, particularly for trimming (smoothing) an object part on the surface of cartilages such as a shoulder, hip joint and knee.

Figure 15:
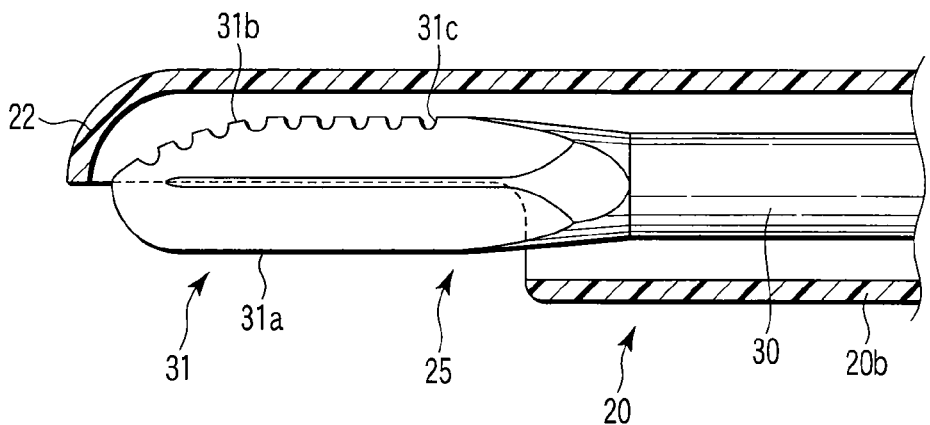
FIG. 15 is a schematic diagram of peripheral parts of a treatment portion in a first modification of the second embodiment.

Next, a first modification of this embodiment will be explained with reference to FIG. 15.

Figure 5A:
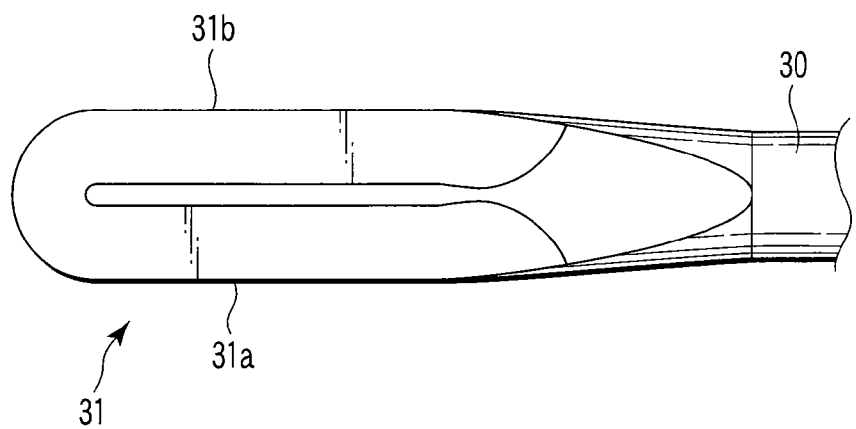
FIG. 5A is a side view of a treatment portion.
Figure 5B:
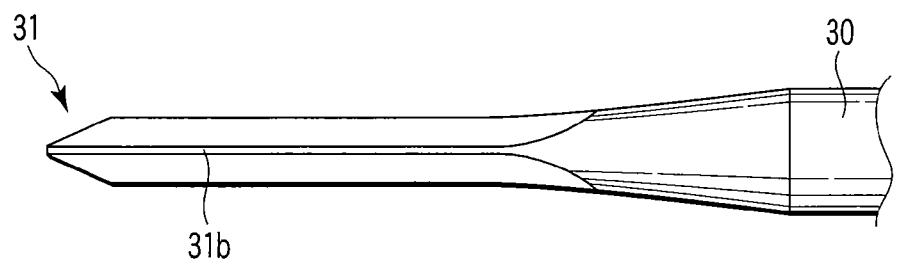
FIG. 5B is a top view of the treatment portion shown in FIG. 5A.
Figure 5C:
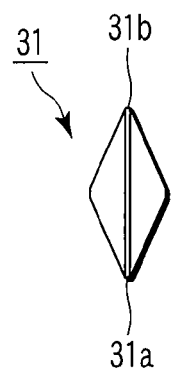
FIG. 5C is a front view of the treatment portion shown in FIG. 5A.

The shape of the treatment portion 31 of this modification is different from the treatment portion 31 of the second embodiment. The treatment portion 31 of this modification is formed to have a substantially flat part as shown in FIGS. 4 and 5 in the first embodiment, and a substantially flat part with a pointed distal end as shown in FIGS. 8A to 8C in the first modification of the first embodiment.

In this modification, the first edge 31a side is substantially flat, and the second edge 31b side is substantially flat with a pointed distal end, having semicircular recesses 31c at equal intervals. The radius of the recess 31c and the pitch between adjacent recesses 31c are substantially the same as the first modification of the first embodiment.

Therefore, this modification can provide the same operations and effects as those of the second embodiment.

Next, a second modification of this embodiment will be explained with reference to FIGS. 16 and 17.

The treatment portion 31 of this modification has only the first treatment surface 46a having square pyramid-shaped serrations 45a.

In this modification, when the stopper 26b fits in the recess 21a, the first treatment surface 46a is exposed to the open part 25, and the surface 46b other than the first treatment surface 46a is retracted into the distal end member 20b. When the stopper 26b fits in the recess 21b, the first treatment surface 46a is retracted into the distal end member 20b, and the surface 46b is exposed to the open part 25, as shown in FIG. 17. As the surface 46b do not have the serrations 45a, even when the surface 46b contacts an object part of a living body tissue, the object part is not ultrasonically operated on.

As the sheath 20 is rotationally moved in the peripheral direction of the probe 30 insertion direction (the longitudinal axis 5), the treatment portion 31 is moved to the state exposed to the open part 25 for carrying out a surgical treatment on an object part by the ultrasonic vibration transmitted from the probe 30, or the state retracted into the sheath 20 as a standby state without carrying out a surgical treatment on an object part.

Next, an explanation will be given on operating treatments in this modification. The treatments other than those explained here are almost the same as those in the first embodiment, and detailed explanation thereof is omitted.

Figure 16:
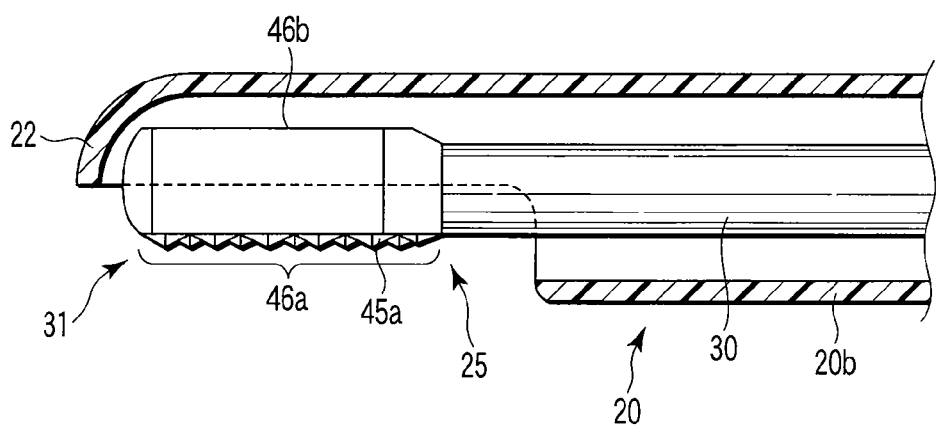
FIG. 16 is a schematic diagram of peripheral parts of a treatment portion in a second modification of the second embodiment.

As shown in FIG. 16, the first treatment surface 46a is exposed to the open part 25. In this state, the first treatment surface 46a is made to contact an object part of a living body tissue. When the probe 30 ultrasonically vibrates, the first treatment surface 46a ultrasonically operates on the contacting object part.

Figure 17:
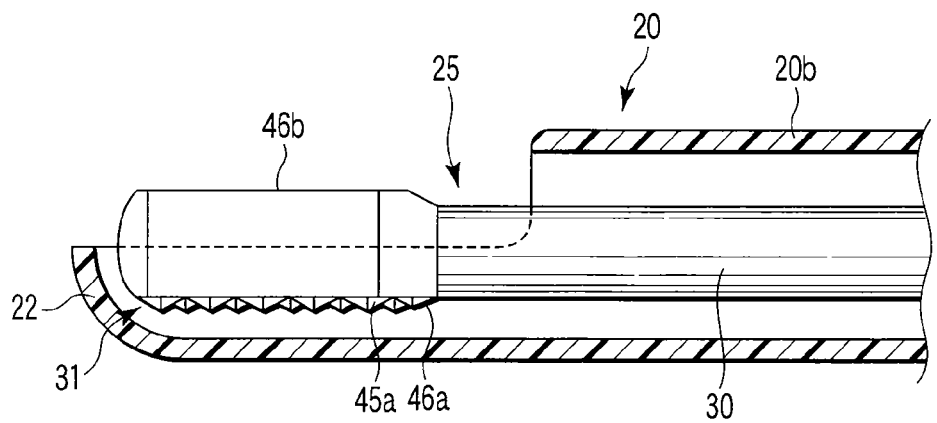
FIG. 17 is a cross sectional view of the treatment portion with a distal end member moved from the state shown in FIG. 16.

Further, as explained in the first embodiment, when the sheath 20 is rotationally moved about 180 degrees from the state shown in FIG. 16 as in the first embodiment, the first treatment surface 46a is retracted into the distal end member 20b as shown in FIG. 17, and the surface 46b is exposed to the open part 25. Even if the hand switch 15 or foot switch 70 is mistakenly operated in this state, an object part is not ultrasonically operated on. Namely, the treatment portion 31 stays in a standby state.

As described above, in this modification, by setting the treatment portion 31 to a standby state, it is possible to prevent damages of an unexpected part of a living tissue except for an object part by erroneous operation of the hand switch 15 or foot switch 70. Therefore, this modification improves safety.

Next, a third modification of this embodiment will be explained with reference to FIGS. 18A to 18C, 19, and 20.

Figure 18A:
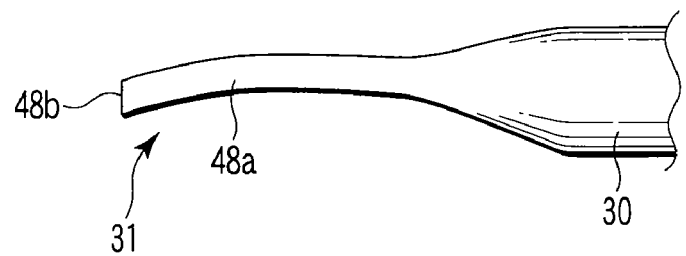
FIG. 18A is a side view of a treatment portion in a third modification of the second embodiment.
Figure 18B:
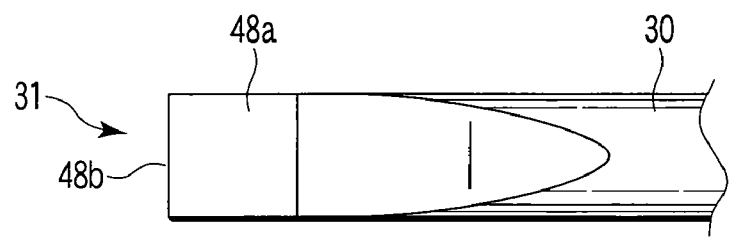
FIG. 18B is a top view of the treatment portion shown in FIG. 18A.
Figure 18C:
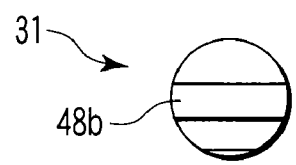
FIG. 18C is a front view of the treatment portion shown in FIG. 18A.
Figure 21:
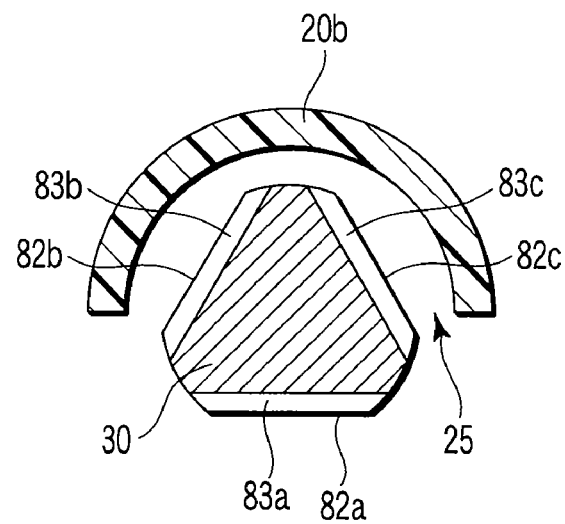
FIG. 21 is a cross sectional view of peripheral parts of the treatment portion in a fourth modification of the second embodiment.

The shape of the treatment portion 31 of this modification is different from the treatment portion 31 of the second embodiment. As shown in FIGS. 18A to 18C, the treatment portion 31 is shaped substantially flat, and curved toward the distal end portion 48a. The distal end portion 48a has a treatment end surface 48b for ultrasonically carrying out a surgical treatment on an object part.

When the sheath 20 is rotationally moved around the probe 30, the treatment portion 31 is moved to the state exposed to the open part 25 for carrying out a surgical treatment on an object part by the ultrasonic vibration transmitted from the probe 30, or the state retracted into the sheath 20 as a standby state without carrying out a treatment on an object part.

As shown in FIG. 19, the treatment end face 48b is exposed to the open part 25. In this state, the treatment end face 48b is made to contact an object part of a living tissue. When the probe 30 ultrasonically vibrates, the treatment end face 48b ultrasonically operates on the contacting object part.

Further, as explained in the first embodiment, when the sheath 20 is rotationally moved about 180 degrees from the state shown in FIG. 19 as in the first embodiment, the treatment end face 48b is retracted into the distal end member 20b as shown in FIG. 20.

Even if the hand switch 15 or foot switch 70 is mistakenly operated in this state, the treatment end face 48b is retracted into the distal end member 20b, and ultrasonic vibration is not transmitted to an object part through the treatment end face 48b. Thus, an object part is not ultrasonically operated on. Namely, the treatment portion 31 stays in a standby state.

As described above, in this modification, by setting the treatment portion 31 to a standby state, it is possible to prevent damages of an unexpected part of a living tissue except for an object part by erroneous operation of the hand switch 15 or foot switch 70. Therefore, this modification improves safety.

Next, a fourth modification of this embodiment will be explained with reference to FIGS. 21 to 25.

Figure 22:
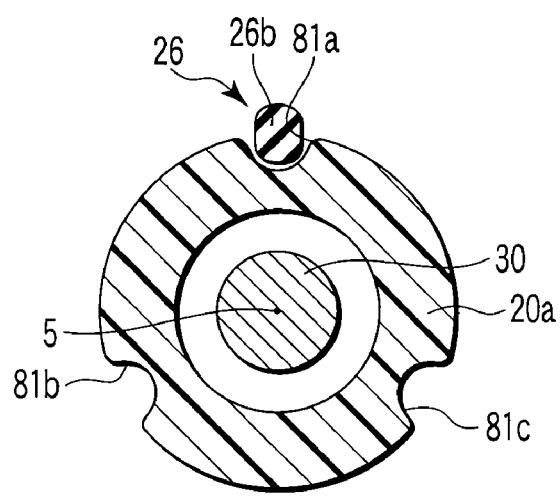
FIG. 22 is a cross sectional view of a main body in the fourth modification of the second embodiment.

As shown in FIG. 22, a main body 20a of this modification has recesses 81a, 81b and 81c to fit with the stopper 26b. The recesses 81a, 81b and 81c are arranged at equal intervals in the peripheral direction of the longitudinal axis 5. Namely, the recesses 81a, 81b and 81c are apart about 120 degrees in the peripheral direction of the longitudinal axis 5.

Further, as shown in FIGS. 23 to 25, the shape of the treatment portion 31 of this modification is different from the treatment portion 31 of the second embodiment.

The treatment portion 31 has a first treatment surface 82a corresponding to the recess 81a, a second treatment surface 82b corresponding to the recess 81b, and a third treatment surface 82c corresponding to the recess 81c.

When the stopper 26b fits in the recess 81a, the first treatment surface 82a is exposed to the open part 25, and the second and third treatment surfaces 82b and 82c are retracted into the distal end member 20b, as shown in FIG. 23.

When the stopper 26b fits in the recess 81b, the second treatment surface 82b is exposed to the open part 25, and the first and third treatment surfaces 82a and 82c are retracted into the distal end member 20b, as shown in FIG. 24.

When the stopper 26b fits in the recess 81c, the third treatment surface 82c is exposed to the open part 25, and the first and second treatment surfaces 82a and 82b are retracted into the distal end member 20b, as shown in FIG. 25.

When any one of the first, second and third treatment surfaces 82a, 82b and 82c is made to contact an object part, the treatment portion 31 ultrasonically operates on an object part.

The first, second and third treatment surfaces 82a, 82b and 82c have serrations 83a, 83b and 83c having triangular cross sections. The serrations 83a, 83b and 83c are formed in the direction along the longitudinal axis 5.

The serrations 83a are larger than the serrations 83b.

Further, in general, the amplitude of ultrasonic vibration is gradually decreased from the distal end to proximal end of the probe 30. Here, the serrations 83c are formed to reduce in size (a pitch between serrations 83c) from the distal end side to proximal end side of the probe 30. Namely, the serrations 83c are formed to reduce in size substantially proportional to the amplitude of ultrasonic vibration.

As described above, the treatment portion 31 has two or more treatment surfaces (the first treatment surface 82a, second treatment surface 82b, and third treatment surface 82c) in the peripheral direction of the probe 30 insertion direction (in the direction of the longitudinal axis 5). Further, as the sizes of the serrations 83a, 83b and 83c are different, the treatment portion 31 has two or more different size treatment surfaces.

Next, an explanation will be given on operating treatments in this embodiment. The treatments other than those explained here are almost the same as those in the first embodiment, and detailed explanation thereof is omitted.

When the stopper 26b fits in the recess 81a, the first treatment surface 82a is exposed to the open part 25, and ultrasonically operates on an object part.

When the sheath 20 is rotationally moved about 120 degrees from the state shown in FIG. 23, the stopper 26b fits in the recess 81b, the second treatment surface 82b is exposed to the open part 25 as shown in FIG. 24, and ultrasonically operates on an object part.

When the sheath 20 is rotationally moved by another 120 degrees from the state shown in FIG. 24, the stopper 26b fits in the recess 81c, and the third treatment surface 82c is exposed to the open part 25, as shown in FIG. 25, and ultrasonically operates on an object part.

The serrations 83c are formed to be substantially proportional to the amplitude of ultrasonic vibration. Therefore, surgery with the serrations 83c in the distal end side is rough cutting, and surgery with the serrations 83c in the proximal end side is finish cutting.

Therefore, this embodiment can provide the same effects as the second embodiment described above.

The invention is not limited to the embodiments described herein. The invention may be embodied in a practical stage by modifying the constituent elements without departing from its essential characteristics. The invention may also be embodied by appropriately combining the constituent elements disclosed in the embodiments described herein.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic surgical instrument for cutting or shaving hard tissues, comprising:
    an ultrasonic transducer for producing ultrasonic vibration;
    a case for storing the ultrasonic transducer;
    a transmission member which has a distal end portion and a proximal end portion, connects the ultrasonic transducer in the proximal end portion, and transmits the ultrasonic vibration produced by the ultrasonic transducer from the proximal end portion to the distal portion; and
    a sheath which covers the transmission member and connects the case movably along a peripheral direction of the transmission member,
    wherein the transmission member has a treatment portion in the distal end portion,
    the treatment portion has at least a first treatment portion and a second treatment portion provided in positions different from each other in the peripheral direction of the transmission member,
    the sheath is provided in a position corresponding to the treatment position, and has an open part in which one of the first treatment portion and the second treatment portion is exposed, and when the sheath is rotationally moved along the peripheral direction of the transmission member to the transmission member, the treatment portion is switched to one of a first state in which the first treatment portion is exposed via the open part and the second treatment portion is covered by the sheath when the first treatment portion cuts or shaves hard tissues, and a second state in which the second treatment portion is exposed via the open part and the first treatment portion is covered by the sheath when the second treatment portion cuts or shaves hard tissues.

2. The ultrasonic surgical instrument according to claim 1, wherein the sheath includes a cold knife at least a distal end of the sheath.

3. The ultrasonic surgical instrument according to claim 1, wherein the sheath includes a high frequency electrode at least a distal end of the sheath.

4. The ultrasonic surgical instrument according to claim 1, further comprising a positioning mechanism for controlling the rotation of the sheath to the case to position the sheath to the case such that the treatment portion is switched to one of the first state and the second state.

5. The ultrasonic surgical instrument according to claim 4, wherein the positioning mechanism has a stopper which is provided at one of the case and the sheath, and a receiver which is provided at the other of the case and the sheath and fits the stopper.

* * * * *